United States Patent [19]

Louarn

[11] 4,316,130

[45] Feb. 16, 1982

[54] PNEUMATIC DEVICE TO CONTROL THE SPEED OF AN ELECTRIC MOTOR

[75] Inventor: Marcel Louarn, Le Lion d'Angers, France

[73] Assignee: Kollmorgen Technologies Corporation, Dallas, Tex.

[21] Appl. No.: 149,647

[22] Filed: May 14, 1980

[30] Foreign Application Priority Data

May 29, 1979 [FR] France ............................. 79 13657

[51] Int. Cl.³ ............................................ H02P 5/16
[52] U.S. Cl. ................................ 318/551; 318/345 F; 318/481
[58] Field of Search ............... 318/551, 481, 645, 335, 318/653, 345 F; 200/86 A, 86.5; 336/87, 30, 20; 323/51

[56] References Cited

U.S. PATENT DOCUMENTS

| 2,980,837 | 4/1961 | Wu | 336/30 |
|---|---|---|---|
| 3,469,164 | 9/1969 | Truemper et al. | 323/51 |
| 3,509,485 | 4/1970 | Czerny | 336/87 |
| 3,555,405 | 1/1971 | Martin | 323/51 |
| 3,593,086 | 7/1971 | Thombs | 318/308 |
| 3,735,244 | 5/1973 | Gumtau et al. | 323/51 |
| 3,818,292 | 6/1974 | Berman | 318/139 |
| 3,848,180 | 1/1974 | Jonice et al. | 336/20 |
| 4,624,484 | 5/1977 | Tomczak et al. | 336/30 |

Primary Examiner—David Smith, Jr.
Attorney, Agent, or Firm—Morgan, Finnegan, Pine, Foley & Lee

[57] ABSTRACT

Device to control the speed of an electric motor from a pneumatic pedal, characterized in that it includes an element deformable with the pressure controlled by the pneumatic pedal, an element of magnetic material forming a mechanical unit with the element deformable with the pressure and capable of modifying the inductance of a coil incorporated into an electronic control circuit for the current of the electric motor the speed of which is to be controlled.

5 Claims, 4 Drawing Figures

PNEUMATIC DEVICE TO CONTROL THE SPEED OF AN ELECTRIC MOTOR

This invention is concerned with motor controls and, more particularly, with a pneumatic control for controlling the speed of a variable speed electric motor.

In some facilities, for example, a dentist's office, it is common in the performance of certain work or procedures to use both pneumatic equipment, such as turbines or air motors, and electrical motors to drive certain types of equipment and to use such equipment successively or simultaneously.

In general, in such pneumatic equipment, air to the air driven equipment is controlled by a pedal depressed and released by the foot of the operator or practitioner. Thus, to deliver more air to, and thus speed up the equipment, the practitioner pushes or depresses the control pedal and, to deliver less air to, and thus slow down the equipment, the practitioner releases or allows the pedal to rise, such as, e.g., by a spring, compressed as the pedal was depressed. Where electrical equipment is also used, up to now, the practitioner must use a second, electrical, pedal to control the speed of the electrical motor. Thus, when the practitioner switches operation from one type of equipment to the other, he must go from one pedal to the other and disrupt the work or procedure being performed. The use of two pedals is not only inconvenient but complicated, and adds to the cost of installation.

The invention of the present application overcomes the deficiencies of the two pedal system by adding to the control system, i.e., the pneumatic pedal, an inexpensive pressure-to-voltage conversion device, which allows a single pedal of the pneumatic type to be adapted and used to control both the pneumatic and the electrical drive systems.

This goal is attained by means of a device to control the speed of an electric motor from a pneumatic pedal, characterized in that the device includes an element deformable with the pressure controlled by the pneumatic pedal, an element of magnetic material forming one mechanical unit with the element deformable with the pressure and capable of modifying the inductance of a coil incorporated into an electronic control circuit for controlling the current to the electric motor and thus the speed of the motor.

Other characteristics and advantages of the invention will be more apparent from the following description of a particular mode of application of the invention, given solely as a non-limitative example, in reference to the appended drawings.

Figure 1:
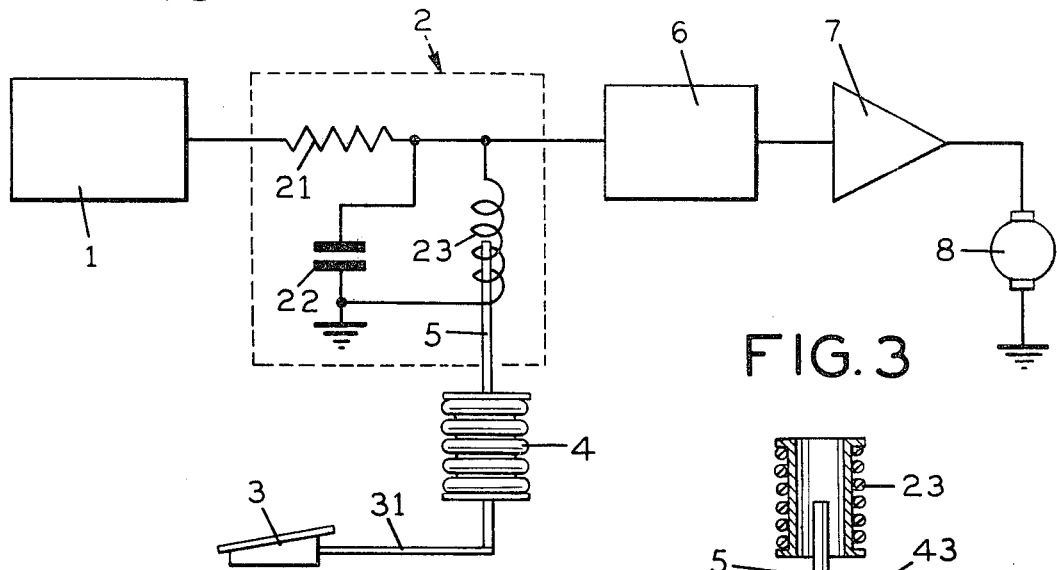
FIG. 1 is a schematic diagram of an electric motor speed control device, by pneumatic pedal, according to the invention.

Referring to FIG. 1, the speed of electric motor 8 is controlled by the operation of pneumatic pedal 3. Pedal 3 modifies the pressure inside element 4 and causes bellows 42 and spring 43 to expand. Rod 5 of magnetic material, such as ferrite, is mechanically attached to element 4 and penetrates into coil 23 incorporated in circuit 2 of an anti-resonant circuit type. Oscillator 1 feeds trap-circuit 2 which is connected with circuit 6. This circuit delivers a D.C. signal proportioned to the output amplitude of circuit 2. The output of circuit 6 is connected to amplifier 7 which, in turn, is connected with the motor 8, thus controlling the speed of said motor 8 as a function of the position of rod 5 and thus of the position of pedal 3 (FIG. 1).

Figure 2:
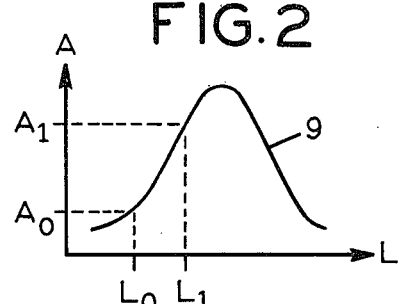
FIG. 2 is an electrical characteristic diagram of the operation of a part of the circuits of the device according to the invention.

In FIG. 2, curve 9 represents the variation in the output amplitude of circuit 2 in relation to the inductance of said circuit. The inductance of circuit 2 increases as bellows 42 and spring 43 expand and rod 5 is projected into coil 23 (FIG. 3).

When the practitioner pushes on pedal 3, bellows 4 (FIG. 1) expands with the air pressure thus provided to said bellows 4. This expansion causes rod 5 to penetrate into coil 23. In the absence of pressure, rod 5 penetrates very little into coil 23. Said coil, therefore, exhibits an inductance of value Lo and the amplitude of the signal at the output of circuit 2 has a value Ao. Lo, Ao are the coordinates of a point on curve 9. When pedal 3 is depressed, the expansion of element 4 causes rod 5 to penetrate further into coil 23, and the point of operation on curve 9 becomes the point of coordinates L1 and A1. In relation to Ao, the amplitude A1 is much greater.

Figure 3:
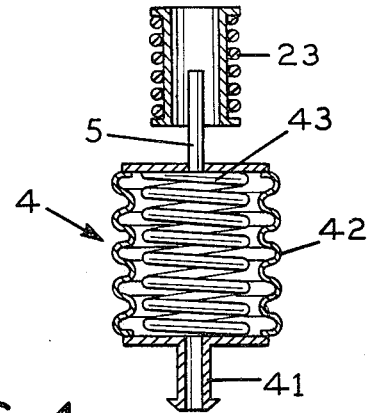
FIG. 3 is a detail representation of the mobile part of the invention.

FIG. 3 is a sectional representation of the deformable element 4. Element 4 includes a metal bellows 42 provided with air inlet 41, which air inlet 41 is connected to pedal 3 by tube 31 (FIG. 1). On the inside, attached to the two ends of bellows 42, is spring 43. The stiffness of spring 43 allows the deformation of bellows 42 to be adapted to different ranges of inlet air pressure. The magnetic material attached to bellows 42 is a ferrite rod 5 which penetrates more or less deeply into coil 23 of circuit 2 (FIG. 1) to cause the inductance of coil 23 to vary.

Figure 4:
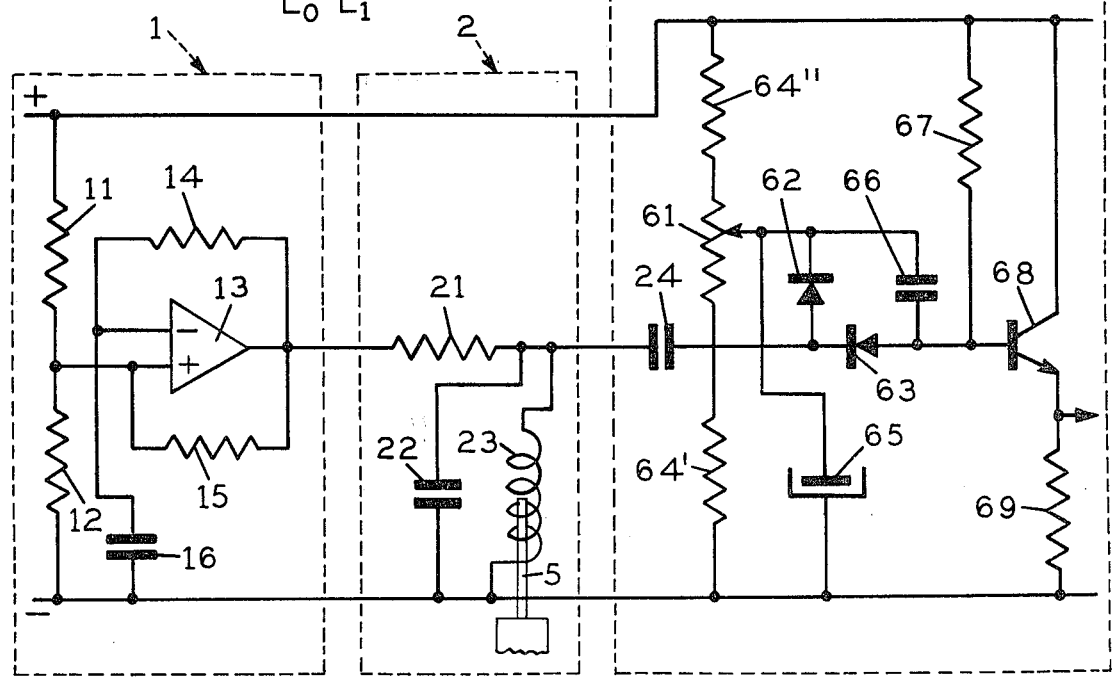
FIG. 4 is a bloc-diagram of an example of the electronic circuit employed in the device according to the invention.

FIG. 4 represents a particular example of an electronic circuit allowing the speed of motor 8 to be controlled by using a pneumatic pedal adapted in accordance with the present invention to adjust circuit 2.

In FIG. 4, oscillator 1 is composed of an operational amplifier 13 arranged as an astable multivibrator and is connected to circuit 2. Input 13' of operational amplifier 13 is connected to power supply lines + and —, respectively, by resistors 11 and 12, and input 13'' to the negative power supply line by capacitor 16. Resistors 14 and 15 are connected between the output terminal 13''' of operational amplifier 13 and, respectively, its input terminals 13' and 13''. The output of oscillator 1 is connected to circuit 2 through resistor 21 which, in turn, is connected to capacitor 22 and inductance 23, arranged in parallel to form the trap-circuit.

Rectifier circuit 6, connected to the output of anti-resonant circuit 2 through a linking capacitor 24, includes a resistor bridge consisting of resistors 64' and 64'' with a threshold-adjustment potentiometer 61, two diodes 62 and 63, capacitors 65 and 66 an transistor 68 connected to the power supply lines by resistors 67 and 69. The output signal from amplifier 7 (FIG. 1) is applied to the emitter of transistor 68. The output of amplifier 7 is connected to and controls the speed of the electric motor 8 (FIG. 1).

It should be obvious that there are numerous variations and modifications within the scope of the present invention, which is more particularly defined in the appended claims.

What is claimed:

1. A device for controlling the speed of an electric motor from a pneumatic pressure control means, characterized in that it comprises a pneumatic pressure control means; an element deformable with the pressure controlled by said pressure control means which includes metal bellows having a pressure inlet, and spring means incorporated on the inside or outside of said bellows and attached to them to permit a predetermined deformation of said bellows in relation to said pressure, and a rod of magnetic material attached to and moving with the deformation of said bellows; an inductance oil; an element of magnetic material attached to and forming one mechanical unit with said pressure deformable element, and aligned with said inductance coil for modifying the inductance of said inductance coil as a function of the deformation of the deformable element as said magnetic element is advanced into or retracted from said coil; said inductance coil forming part of tunable trap circuit means; further comprising oscillator means connected to the input of said tunable circuit means; and rectifier means connected to the output of said tunable circuit means for providing a D.C. signal of an amplitude being a function of the deformation of said deformable element and thus of the pressure provided by said pressure control means; and amplifier means connected to the output of said rectifier means and energizing, and thus controlling the speed of said electric motor.

2. The device for controlling the speed of an electric motor as claimed in claim 1 wherein the pressure control means is a pneumatic pedal.

3. The device as claimed in claim 1 or 2 wherein the pressure controlled by the pressure control means is air pressure.

4. The device, as recited in claim 1, 2 or 3, characterized in that said element of magnetic material is a dipping core which penetrates said coil in relation to the deformation of said bellows.

5. The device, as recited in claim 1, 2, 3 or 4, wherein said element of magnetic material consists of ferrite rod.

* * * * *